United States Patent [19]

Daniels et al.

[11] 4,178,453
[45] Dec. 11, 1979

[54] PROCESS FOR THE PREPARATION OF 2,5-DIDEOXYSTREPTAMINE AND OF A NOVEL INTERMEDIATE THEREFOR

[75] Inventors: Peter J. L. Daniels, Cedar Grove; Mohammed M. N. Varchei, North Caldwell, both of N.J.

[73] Assignee: Schering Corporation, Kenilworth, N.J.

[21] Appl. No.: 869,207

[22] Filed: Jan. 13, 1978

Related U.S. Application Data

[62] Division of Ser. No. 443,051, Feb. 15, 1974, Pat. No. 4,092,359.

[51] Int. Cl.$^2$ ............................................ C07D 231/00
[52] U.S. Cl. .................................. 548/369; 260/563 R
[58] Field of Search ..................... 260/563 R; 548/369

[56] References Cited

U.S. PATENT DOCUMENTS 3,637,738  1/1972  Gschwend et al. .................. 548/369

Primary Examiner—Paul F. Shaver
Attorney, Agent, or Firm—Raymond A. McDonald

[57] ABSTRACT

The aminocyclitol 2,5-dideoxystreptamine may be prepared by a novel two-step synthesis from cis-4,8-dioxatricyclo [5.1.0.0$^{3,5}$]octane. The aminocyclitol and a novel intermediate in the synthesis thereof are utilized by a *Micromonospora inyoensis* (*M. inoyensis* strain 1550F-1G NRRL 5742) for the elaboration of a novel antibacterial agent designated Mutamicin 2.

2 Claims, No Drawings

PROCESS FOR THE PREPARATION OF 2,5-DIDEOXYSTREPTAMINE AND OF A NOVEL INTERMEDIATE THEREFOR

This is a division of application Ser. No. 443,051, filed Feb. 15, 1974 now U.S. Pat. No. 4,092,359.

This invention relates to 6,7,-diaza-2,4-dihydroxybicyclo [3.2.1] octane and 2,5-dideoxystreptamine. More particularly, this invention relates to the above named novel compounds and to a novel chemical process for the preparation thereof wherein cis 4,8-dioxatricyclo [5.1.0.0$^{3,5}$] octane (hereinafter cis 1,4-cyclohexadiene dioxide) is utilized as the starting compound. This invention also relates to acid addition salts of the compounds and to methods for preparing said salts.

PRIOR ART

Many aminoglycoside antibiotics contain subunits which are aminocyclitols. The aminocyclitol most frequently encountered as a subunit is 2-deoxystreptamine, the compound being one of the subunits of gentamicin, kanamycin, neomycin, paromomycin, and sisomicin. Recently, W. Thomas Shier and coworkers in the Proceedings of the National Academy of Science 63:198–204 (1969), reported that strains of certain microorganisms could utilize certain aminocyclitols to produce antibiotics, some of which are novel.

However, in order to effect such a process, it is necessary to devise methods for synthesing the aminocyclitols since many of the ones already known in the art are produced as a subunit of an antibiotic and are available only by degradation of an aminocyclitol antibiotic which would render the aminocyclitol prohibitively expensive.

The preparation of cis 1,4-cyclohexadiene dioxide, the starting material for the synthesis of the compounds of this invention, is described in a paper by Craig, T. W. et al. in the Journal of Organic Chemistry, Vol. 32, pages 3743–3749 (1967).

In an application by M. J. Weinstein et al. entitled, "New Antibiotics Produced by Micromonospora Mutants" Ser. No. 443,052, being filed concurrently herewith, is described a process by which *Micromonospora inyoensis* strain 1550F-1G NRRL 5742 utilizes 2,5-dideoxystreptamine to prepare a novel antibiotic designated mutamicin 2.

Mutamicin 2 is a broad spectrum antibiotic having the following structure, the 2,5-dideoxystreptamine subunit being the one shown in the upper right side of formula I.

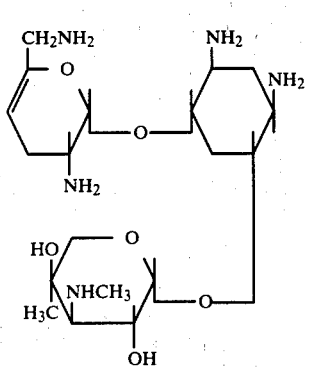

I

Since Mutamicin 2 is a broad spectrum antibacterial agent, it may be used to inhibit or destroy susceptible bacteria and is especially useful in admixture with soaps and detergents for cleaning hospital equipment and laboratory glassware.

As stated above, when 2,5-dideoxystreptamine is added to a fermentation medium containing *Micromonospora inyoensis* strain 1550F-1G NRRL 5742 and a assimilable source of carbon and nitrogen, as described in the above-mentioned patent application, said mutant produces Mutamicin 2. In the absence of 2,5-dideoxystreptamine or other aminocyclitol, the aforesaid mutant produces no detectable quantity of antibiotic. Therefore, this compound is necessary intermediate for the production of Mutamicin 2 and may also be used as a building block in other biosynthetic or chemical syntheses.

SUMMARY AND DESCRIPTION OF THE INVENTION

The invention sought to be patented may be described as a two-stage process for preparing 2,5-dideoxystreptamine (II)

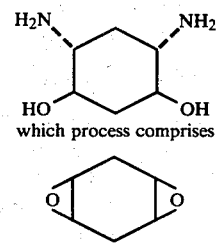

II which process comprises

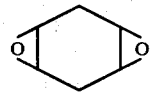

III (A) Treating cis-1,4-cyclohexadiene dioxide (III) with hydrazine to form 6,7-diaza-2,4-dihydroxybicyclo [3.2.1] octane (IV), (B) hydrogenolyzing said compound (IV) to form 2,5-dideoxystreptamine (II) and optionally converting the product to an acid addition salt.

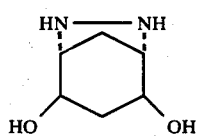

IV

The process of Step A is advantageously effected at elevated temperatures such as, at the boiling points of such organic solvents as toluene, xylene, 2-ethoxyethanol or preferably, 2-methoxyethanol. Further, the reaction is preferably effected in the presence of anhydrous magnesium sulfate which acts as a dehydrating agent and may serve as a complexing agent which promotes the opening of the epoxide in the desired configuration. Additionally, the reaction is usually effected for from about 18 to about 28, preferably about 24 hours in an inert atmosphere preferably under nitrogen or argon. Thus, the compounds of this invention embrace 2,5-dideoxystreptamine, and the acid addition salts thereof. Also embraced herein are 6,7-diaza-2,4-dihydroxybicyclo [3.2.1] octane and acid addition salts of this compound.

The process of steb B is advantageously effected at ambient temperature and above atmospheric pressure for from about 18 to 28, preferably 24 hours. Further, the reaction is most economically effected using water as the solvent. However, mixtures of water and water miscible organic solvents which are inert to catalytic hydrogenation, such as alcohols, may also be used. The catalysts employed in the reaction may be the metal catalysts usually employed for hydrogenation or hydrogenolysis reactions such as palladium, platinum, rhodium, or preferably Raney Nickel.

The compounds of this invention are generally used in the form of the free nitrogen base but may be used in the form of salts of acids such as the mineral acids, hydrocarbon carboxylic acids or alkyl, aryl or aralkyl sulfonic acid or the like. The formation of such acid addition salts is usually effected in the conventional manner such as, by the addition of an excess of acid to a solution of the free base and the precipitation of the salt by the addition of a precipitating agent. Further, the formation of such salts facilitates the isolation and purification of the novel compounds of this invention.

The following examples set forth the best mode contemplated by applicants for carrying out the instant invention:

EXAMPLE 1

2,5-Dideoxystreptamine Dihydrochloride

A. 6,7-Diaza-2,4-dihydroxybicyclo [3.2.1] octane

Combine and heat at reflux with stirring under an inert atmosphere ($N_2$ or argon) for 24 hours 70 g. of cis-1,4-cyclohexadiene dioxide, 80 ml. of hydrazine hydrate and 80 g. of anhydrous magnesium sulfate in 7000 ml. of 2-methoxy-ethanol. Remove the solvent under reduced pressure and extract the residue with hot methanol (1500 ml.). Evaporate the methanol to give the product as a white crystalline solid.

Yield 75 g., m.p. 199°–200° (dec.).

Analysis: Calculated for $C_6H_{12}N_2O_2$: C, 49.85; H, 8.25; N, 19.40%. Found: C, 50.15; H, 8.59; N, 19.33%.

B. 2,5-Dideoxystreptamine

Hydrogenate 100 mg. of the product of step A in the 30 ml. of water at 42 p.s.i over 20 mg. of a Raney Nickel catalyst for 24 hours. Remove the catalyst and evaporate the solvent under reduced pressure affording 2,5-dideoxystreptamine.

Yield 100 mg., m.p. 187° (dec.).

C. 2,5-Dideoxystreptamine Dihydrochloride

Prepare a solution of 73 mg. of 2,5-dideoxytstreptamine in 5 ml. of water, add 1.1 ml. of 1 N hydrochloric acid solution stir for 10 minutes. Lyophilize the resulting solution and obtain thereby 106 mg. of the title compound which upon crystallization from aqueous ethanol affords substantially pure 2,5-dideoxystreptamine dihydrochloride, m.p. 340° C.

Analysis: Calculated for: $C_6H_{14}N_2O_2 \cdot 2HCL$: C, 32.88; H, 7.37; N, 12.78%. Found: C, 32.73; H, 7.24; N, 12.31%.

We claim:

1. A compound of the formula:

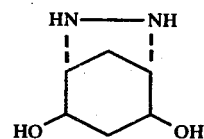

and the non-toxic acid addition salts thereof.

2. An acid addition salt of 6,7-diaza-2,4-dihydroxybicyclo [3.2.1] octane.

* * * * *